United States Patent
Liu et al.

(10) Patent No.: US 7,173,170 B2
(45) Date of Patent: Feb. 6, 2007

(54) **HIGH THREONINE PRODUCING LINES OF *NICOTIANA TOBACUM* AND METHODS OF PRODUCING**

(75) Inventors: Wennuan Liu, Clemmons, NC (US); Michael Francis Dube, Winston-Salem, NC (US); Luis Mayan Dominguez, Winston-Salem, NC (US); Jerry Wayne Lawson, Pfafftown, NC (US)

(73) Assignee: Reynolds Technologies, Inc., Winston-Salem, NC (US)

( * ) Notice: Subject to any disclaimer, the term of this patent is extended or adjusted under 35 U.S.C. 154(b) by 394 days.

(21) Appl. No.: 10/463,449

(22) Filed: Jun. 17, 2003

(65) Prior Publication Data

US 2005/0005335 A1 Jan. 6, 2005

Related U.S. Application Data

(62) Division of application No. 09/949,973, filed on Sep. 10, 2001, now Pat. No. 6,730,832.

(51) Int. Cl.
*C12N 15/01* (2006.01)
*C12N 15/05* (2006.01)

(52) U.S. Cl. .................. 800/317.3; 800/260; 800/266; 800/268; 800/270; 800/298

(58) Field of Classification Search ............. 800/317.3, 800/260, 266, 268, 270, 298; 435/69.1
See application file for complete search history.

(56) References Cited

U.S. PATENT DOCUMENTS

| 4,407,307 | A | 10/1983 | Gaisch et al. |
| 4,537,204 | A | 8/1985 | Gaisch et al. |
| 5,539,093 | A | 7/1996 | Fitzmaurice et al. |
| 5,668,295 | A | 9/1997 | Wahab et al. |
| 5,670,349 | A | 9/1997 | Cramer et al. |
| 5,705,624 | A | 1/1998 | Fitzmaurice et al. |
| 5,741,898 | A | 4/1998 | Hanley et al. |
| 5,837,876 | A | 11/1998 | Conkling et al. |

FOREIGN PATENT DOCUMENTS

| WO | WO 98/56923 | 12/1998 |
| WO | WO 02/100199 A2 | 12/2002 |

OTHER PUBLICATIONS

Frankard V. et al., Plant Physiology, 1992 vol. 99; pp. 1285-1293.*
Malmberg R. et al., Chapter 2; Production and Analysis of Plant Mutants, Emphasizing *Arabidopsis thaliana* published 1993 by CRC press in Methods of Plant Molecular Biology and Biotechnology; Glick BR and Thompson JE eds.*
Bright, S.W.J. et al., "*Two Genes for Threonine Accumulation in Barley Seeds*", Nature, 299:278-279 (1982).
Bright S.W.J. et al., "*Threonine Accumularion in the Seeds of a Barley Mutant with an Altered Aspartate Kinase*," Biochem. Genet, 20:229-243 (1982).

Cattoir-Reynaerts, A et al., "*Selection and Characterization of Carrot Embryoid Cultures Resistant to Inhibition by Lysine Plus Threonine,*" Biochem. Physiol. Pflanzen, 178:81-90 (1983).
Chen, J. and Ho, C.-T., "*Comparison of Volatile Generation in Serine/Threonine/Glutamine-Ribose/Glucose/Fructose Model Systems,*" J. Argric. Food Chem., 47:643-647 (1999).
Diedrick, T.J. et al., "*Tissue Culture Isolation of a Second Mutant Locus for Increased Threonine Accumulation in Maize,*" Theor. Appl. Genet, 79:209-215 (1990).
Dotson, S. B. et al., "*Lysine-Insensitive Aspartate Kinase in Two Threonine-Overproducing Mutants of Maize,*" Planta, 182:546-552 (1990).
Ellstrand, N.C., "*When Transgenes Wander, Should We Worry?,*" Plant Physiol., 125:1543-1545 (2001).
Falco, S.C., et al., "*Using Bacterial Genes to Engineer Plants with Increased Seed Lysine,*" SIM News, 47:53-57 (1997).
Falco, S.C. et al., "*Transgenic Canola and Soybean Seeds with Increased Lysine,*" Biotechnology, 13:577-582 (1995).
Fehr, W.R., "*Mutation Breeding,*" in Applied Plant Breeding, Chapter 6, pp. 6-1 to 6-30, 2nd Ed., Iowa State University, Ames, IA (1983).
Frankard, V. et al., "*Two Feedback-Insensitive Enzymes of the Aspartate Pathway in Nicotiana Sylvestris,*" Plant Physiol., 99:1285-93 (1992).
Frankard, V. et al., "*High Threonine Producer Mutant of Nicotiana Sylvestris (Spegg. and Comes),*" Theor. Appl. Genet, 82:273-282 (1991).
Galili, G. and Larkins, B.A., "*Enhancing the Content of the Essential Amino Acids Lysine and Threonine in Plants,*" In: Plant Amino Acids in Biochemistry and Biotechnology, B.K. Singh, ed., Marcel Dekker, Inc., New York, pp. 487-507 (1999).
Galili, G., "*Regulation of Lysine and Threonine Synthesis,*" The Plant Cell, 7:899-906 (1995).
Haughn, G.W. and Somerville, C.R., "*Selection for Herbicide Resistance at the Whole Plant Level,*" In: Biotechnology in Agricultural Chemistry, H.M. Lebaron et al. eds (American Chemical Society, Washington, D.C. pp. 98-107 (1987).
Heremans, B. and Jabobs, M., "*Threonine Accumulation in a Mutant of Arabidopsis thaliana (L.) Heynh. with an Altered Aspartate Kinase,*" J. Plant Physiol, 146:249-257 (1995).

(Continued)

Primary Examiner—Russell P. Kallis
(74) Attorney, Agent, or Firm—Kilpatrick Stockton LLP

(57) ABSTRACT

The present invention provides a method for producing plants with a desired phenotypic trait which comprises subjecting plants to mutagenesis, screening chimeric progeny for plants having the desired phenotypic trait, and propagating the survivors. In an embodiment, the phenotypic trait comprises an altered amino acid content. Preferably, the technique is used to generate *Nicotiana tobacum* plant lines having an increase in at least one amino acid. In a preferred embodiment, the invention provides improved *Nicotiana tobacum* plant lines producing at least 1.35 nmole of threonine per milligram of dry plant weight. These plants are useful for improving the flavor and aroma of the tobacco.

11 Claims, 7 Drawing Sheets
(5 of 7 Drawing Sheet(s) Filed in Color)

OTHER PUBLICATIONS

Hibberd, K.A. et al., "*Selection and Characterization of a Feedback-Insensitive Tissue Culture of Maize*," Planta, 148:183-187 (1980).

Karchi, H.J. et al., "*Seed-Specific Expression of a Bacterial Desensitized Aspartate Kinase Increases the Production of Seed Threonine and Methionine in Transgenic Tobacco*," The Plant Journal 3(5):721-727 (1993).

Lea et al., "*The Biosynthesis of Amino Acids in Plants, In: Chemistry and Biochemistry of the Amino Acids*," G.C. Barrett, eds., Chapman & Hill, London, pp. 197-226 (1985).

Lu, G., et al., "*Generation of Flavor Compounds by the Reaction of 2-Deoxyglucose With Selected Amino Acids*," J. Argic. Food Chem., 45:233-236 (1997).

Matthews, B.F., "*Lysine, Threonine and Methionine Biosynthesis*," In: Plant Amino Acids Biochemistry and Biotechnology, B.K. Singh, ed., Marcel Dekker, Inc., New York, pp. 205-225 (1999).

Peng, J. and Harberd, N.P., "*Derivative Alleles of the Arabidopsis Gibberellin-Insensitive (gai) Mutation Confer a Wild-Type Phenotype*," The Plant Cell, 5:351-360 (1993).

Shaul, O. and Galili, G., "*Threonine Overproduction in Transgenic Tobacco Plants Expressing a Mutant Desensitized Aspartate Kinase of Escherichia Coli*," Plant Physiol., 100:1157-1163 (1992).

Williams, J.F. and Gerritsen, B.H., "*Changes in Amino Acid Content of Flue-Cured Tobacco During Natural Aging*," Tobacco Science 128:243-247 (1968).

Van Harten, A.M. "*In: Mutation Breeding*," Chapters 1 and 2, pp. 1-63, Cambridge University Press (1998).

Broun P. and Somerville, C., "*Progress in Plat Metabolic Engineering*," PNAS, 98:8925-8927 (2001).

Malmberg, R. L., "*Production and Analysis of Plant Mutants, Emphasizing Arabidopsis thalian*," Chapter 2, pp. 11-28, CRC Press in Methods of Plant Molecular Biology and Biotechnology: Glick BR and Thompson JE etds. (1993).

* cited by examiner

HIGH THREONINE PRODUCING LINES OF *NICOTIANA TOBACUM* AND METHODS OF PRODUCING

CROSS-REFERENCE TO RELATED APPLICATIONS

This application is a divisional of U.S. patent application Ser. No. 09/949,973, filed Sep. 10, 2001, now U.S. Pat. No. 6,730,832.

FIELD OF THE INVENTION

The present invention relates to a method for producing plants with an altered phenotype, by selection of mutants at the M1 chimeric stage. Specifically, the present invention provides *Nicotiana tobacum* comprising a higher than average threonine content. These plants are useful for developing tobacco blends which have improved taste and aroma.

BACKGROUND OF THE INVENTION

The biosynthesis of amino acids in plants is highly regulated (Lea et al., 1985, *The Biosynthesis of Amino Acids in Plant*, In: Chemistry and Biochemistry of the Amino Acids, G. C. Barrett, ed., Chapman & Hill, London, pp. 197–226). Three essential amino acids, threonine, methionine, and lysine, are produced in plastids from aspartic acid (G. Galili, 1995, *Plant Cell* 7, 899–906; B. F. Matthews, 1999, *Lysine, Threonine, and Methionine biosynthesis*, In: Plant Amino Acids Biochemistry and Biotechnology, B. K. Singh, ed., Marcel Dekker, Inc., New York, pp. 205–225). A key enzyme regulating the biosynthesis of threonine is aspartate kinase (AK). AK catalyzes the phosphorylation of aspartate to form 3-aspartyl phosphate, which is the committed step for the synthesis of threonine, methionine, and lysine (FIG. 1). Subsequently, homoserine dehydrogenase (HSDH), catalyzes the first reaction uniquely associated with threonine and methionine biosynthesis, whereas dihydrodipicolinate synthase (DHDPS) catalyses conversion of 3-aspartyl semialdhehyde to 2,3-dihydrodipicolinate, the first reaction unique to lysine biosynthesis.

High concentrations of threonine and lysine result in feedback inhibition of AK. In addition, high concentrations of threonine and lysine inhibit HSDH and DHDPS, respectively (FIG. 1). It has been reported that plants contain at least three classes of AK isoenzymes, AK-I, AK-II, and AK-III. AK-II and AK-III are both sensitive to threonine inhibition, and AK-I is sensitive to lysine inhibition. Thus, in cells in which normal feedback inhibition pathways are functional, high concentrations of lysine and threonine can cause reduced methionine biosynthesis, such that the synthesis of most enzymes and proteins is reduced.

Due to the general desirability for essential amino acids in grains and other foods, several approaches have been developed to enhance the content of amino acids in plants (see e.g. G. Galili and B. A. Larkins, 1999, *Enhancing the Content of Essential Amino Acids Lysine and Threonine in Plants*, In: Plant Amino Acids in Biochemistry and Biotechnology, B. K. Singh, ed., Marcel Dekker, Inc., New York, pp. 487–507). Also, in tobacco, amino acids are the major, if not the only, nitrogenous source for flavor and aroma production. Amino acids are processed via the Maillard reaction and Stecker Degradation in tobacco to produce pyrazines and other nitrogen containing compounds. The amino acid profile affects not only the yield, but also the type, of pyrazines formed (Lu, G., et. al., 1997, *J. Agric. Food Chem.*, 45: 233–236; J. Chen and C.-T. Ho, 1999, *J. Agric. Food Chem.*, 47: 643–647). For example, even at relatively low concentrations, the hydroxyamino acids threonine and serine yield high molecular weight pyrazines. Amino acids generated by hydrolysis of tobacco proteins can be added to untreated tobacco to make a tobacco having improved flavor and aroma (see e.g., U.S. Pat. Nos. 4,537,204 and 4,407,307). While addition of exogenous amino acids to tobacco (and other plants) is possible, it can result in significant increase in production costs, as well as safety and regulatory concerns as a result of adding of foreign substances to a product for human consumption. Altering the endogenous content of a specific amino acid and/or the profile of the amino acids in tobacco plants would provide a safe, alternative approach to enhance the production of desirable pyrazines necessary for flavor.

Thus, there is a general need for methods that can provide plant lines comprising increased amino acid biosynthesis. The method should be designed so that even for plant species such as tobacco that have a complex genome and thus require screening of a large number of mutation events to isolate the mutation of interest, and are large and thus require extensive facilities for breeding, screening for the desired phenotype is economical. In addition, there is a need to generate tobacco comprising a higher than average free threonine and serine content. By increasing the concentration of threonine and serine, tobacco blends comprising improved taste and aroma are produced.

SUMMARY OF THE INVENTION

The present invention provides line of *N. tobacum* plants having significantly increased levels of threonine and other amino acids. These tobacco plants may be used to generate tobacco products having improved taste and aroma. For example, in an embodiment, tobacco plants of the present invention produce 1.35 nmole of threonine per milligram of dry plant weight, a 6 fold increase over the parent line.

The present invention also comprises an efficient method for plant mutagenesis that provides for an efficient and cost effective plant breeding program. Thus, the present invention includes a mutagenesis step followed by a selection step for M1 chimeric plants. Selection of M1 chimeric plants takes advantage of the fact that in a chimeric plant, cells resistant to the selection agent may confer viability to the entire plant. The present invention eliminates the growth of a large population of M1 plants for production of M2 seeds, and substantially reduces the number of progeny that must be screened at the M2 stage, thereby reducing the time and facilities required for breeding tobacco and other plants.

In one aspect, the present invention comprises a method for producing modified plant lines comprising a predetermined altered phenotype by selection for a mutation of interest in the M1 generation comprising the steps of: incubating seeds for a plant of interest in a solution comprising a mutagen; washing the seeds free of the mutagen; germinating the seeds and growing M1 seedlings; adding a selection agent to the seedlings, wherein the selection agent selects for a chimeric M1 plant, wherein the chimeric M1 plant at least partially comprises the predetermined altered phenotype; growing the M1 chimeric plant to generate M2 seeds, wherein the M2 seeds comprise non-mutagenized M2 seeds and mutagenized M2 seeds comprising the predetermined altered phenotype; and germinating the M2 seeds in a medium containing at least one selection agent to select for M2 plants comprising the predetermined altered phenotype.

In another aspect, the invention comprises a method for producing modified tobacco lines having an increased amount of at least one amino acid comprising the steps of: incubating tobacco seeds in a solution comprising a mutagen; washing the seeds free of the mutagen; germinating the seeds and growing M1 seedlings; adding medium comprising threonine and lysine to the M1 seedlings; growing the M1 seedlings to generate at least one chimeric plant comprising M2 seeds, wherein the M2 seeds from the chimeric plant comprise non-mutagenized M2 seeds and mutagenized M2 seeds; and germinating the M2 seeds in medium containing threonine and lysine to select for the modified tobacco lines.

In one aspect, the present invention comprises a method for improving the flavor of tobacco comprising generating a modified tobacco plant product having an increased concentration of at least one amino acid, mixing the modified tobacco with unmodified tobacco, and including the mixture in the tobacco product.

In another aspect, the present invention comprises a modified tobacco plant having an above-average amount of at least one amino acid as compared to an unmodified parent tobacco line, wherein the genome of the modified tobacco plant consists essentially of plant DNA.

The present invention also comprises a tobacco plant having an above-average amount of at least one amino acid as compared to an unmodified parent tobacco line, wherein the tobacco plant is produced by mutagenesis of tobacco genomic DNA and selection of M1 plants having a mutation of interest.

In another aspect, the present invention comprises a composition comprising a modified tobacco plant having an above-average amount of at least one amino acid as compared to an unmodified parent line, wherein the genome of the modified tobacco plant comprises plant DNA, or wherein the modified tobacco plant is produced by mutagenesis of tobacco genomic DNA and selection of M1 plants having a mutation of interest.

The present invention also comprises an article of manufacture comprising a modified tobacco plant having an above-average amount of at least one amino acid as compared to an unmodified parent tobacco line, wherein the genome of the modified tobacco plant comprises plant DNA or wherein the modified tobacco plant is produced by mutagenesis of tobacco genomic DNA and selection of M1 plants having a mutation of interest.

The present invention also comprises seeds capable of propagating a modified tobacco plant comprising an above-average amount of at least one amino acid as compared to the parent line from which the modified plant is derived.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

Various features, aspects, and advantages of the present invention will become more apparent with reference to the following description, appended claims, and accompanying drawings.

DETAILED DESCRIPTION

Figure 1:
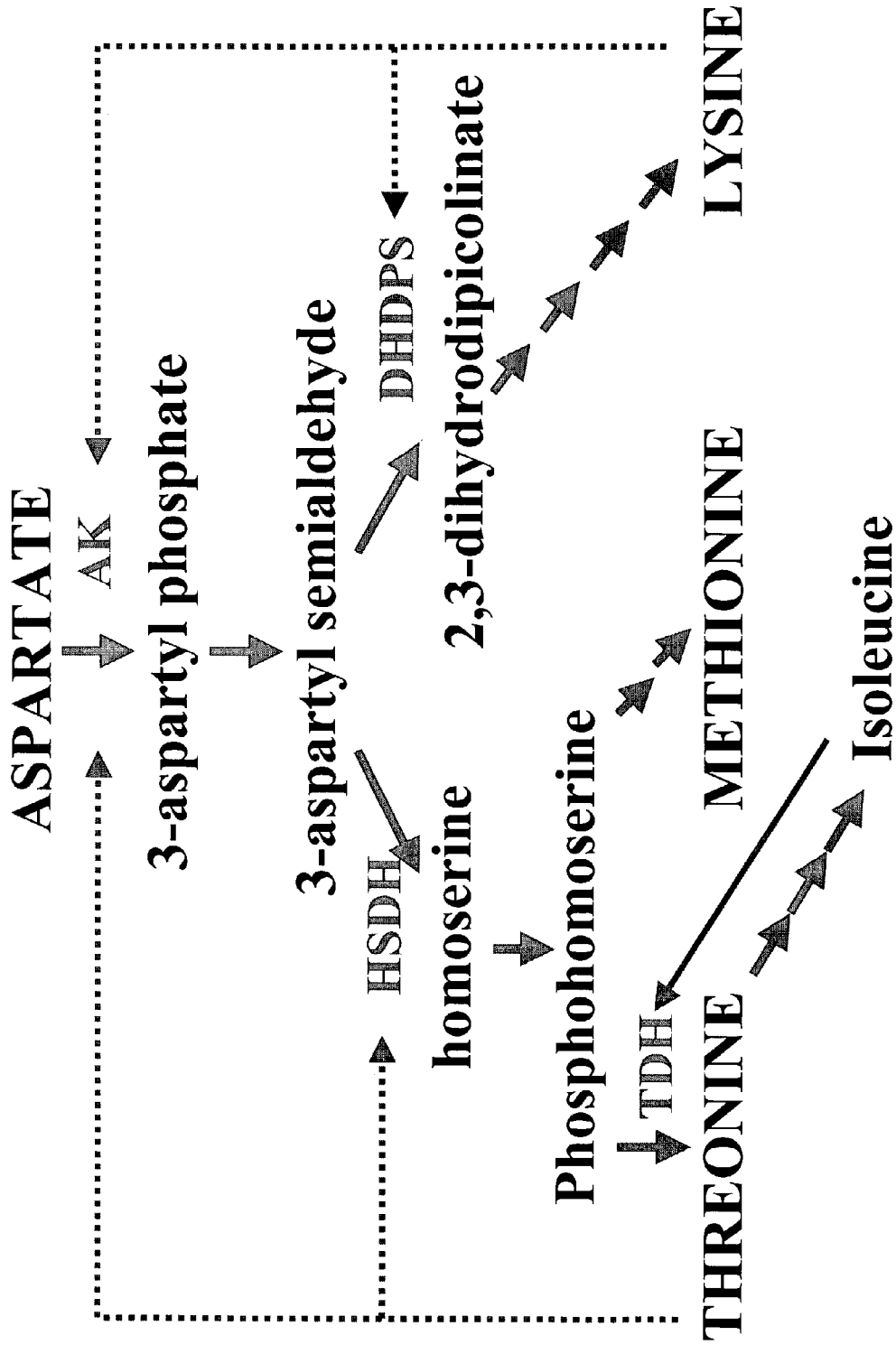
FIG. 1 illustrates key enzymes and points of feedback inhibition of the aspartic acid family biosynthetic pathway, wherein dashed arrows represent feedback inhibition by the end product amino acids, and major enzymes include aspartate kinase (AK), dihydrodipicolinate synthase (DHDPS), homoserine dehydrogenase (HSDH), and threonine dehydratase (TDH).

The present invention comprises a method for plant mutagenesis that includes a selection step at the M1 chimeric stage. For example, in one aspect, the present invention comprises selection of plants comprising resistance to lysine/threonine induced-inhibition of amino acid synthesis. The M1 chimeric plant comprises a subpopulation of cells resistant to the selection agents lysine and threonine; these cells confer viability to the entire plant when the plant is grown in the presence of elevated lysine and threonine. The present invention eliminates the growth of a large population of the M1 plants for production of M2 seeds and, thereby, substantially reduces the number of progeny that must be screened at the M2 stage, thus resulting in a cost-effective plant breeding program suitable for large plants, or plants comprising complex genomes, such as tobacco. The present invention has been used to produce N. tobacum lines comprising a significantly increased amino acid content, and specifically, a significant increase in threonine. These new N. tobacum lines are valuable for making tobacco blends having improved taste and aroma.

In one aspect, the present invention comprises a method for producing a modified plant line comprising a predetermined altered phenotype by selection for a mutation of interest in the M1 generation comprising the steps of: incubating seeds for a plant of interest in a solution comprising a mutagen; washing the seeds free of the mutagen; germinating the seeds and growing M1 seedlings; adding a selection agent to the seedlings, wherein the selection agent selects for a chimeric M1 plant, wherein the M1 chimeric plant at least partially comprises the predetermined altered phenotype; growing the M1 chimeric plant to generate M2 seeds, wherein the M2 seeds comprise non-mutagenized M2 seeds and mutagenized M2 seeds comprising the predetermined altered phenotype; and germinating the M2 seeds in a medium containing at least one selection agent to select for M2 plants comprising the predetermined altered phenotype. Preferably, the invention further comprises growing the M2 plants to generate M3 seeds, wherein at least one of the M2 plants is a heterozygote and at least one of the M2 plants is a homozygote for a mutation causing the altered phenotype and germinating the M3 seeds in medium containing at least one selection agent to identify at least one homozygote M2 plant. Also preferably, the second medium comprising at least one selection agent is added to M1 seedlings at certain developmental stages, as during a predetermined time period after germination.

In an embodiment, the plant line comprises tobacco. Preferably, the tobacco line comprises the genus *Nicotiana*. More preferably, the tobacco line comprises the species *Nicotiana tobacum*. For *N. tobacum*, second medium comprising at least one selection agent is preferably added to M1 seedlings 7 to 14 days after germination. More preferably, the second medium comprising at least one selection agent is preferably added to M1 seedlings about 10 days after germination.

In an embodiment, the mutagen is ethyl methanesulfonate (EMS). Preferably, the EMS comprises a final concentration of 0.01 to 2%. More preferably, the EMS comprises a final concentration of 0.05 to 1%. Even more preferably, the EMS comprises a final concentration of 0.1 to 0.3%. In an embodiment, the mutagenized seeds are suspended in nutrient medium and applied to a semi-permeable surface for growth on liquid medium prior to application of the selection agent.

In an embodiment, the altered phenotype comprises above-average content of at least one amino acid. In an embodiment, to generate plants having an above-average content of at least one amino acid, the selection agent includes threonine. Preferably, the threonine is present at a concentration ranging from 0.3 to 20 mM. More preferably, the threonine is present at a concentration ranging from 0.5 to 10 mM. Even more preferably, the threonine is present at a concentration ranging from 1.0 to 4.0 mM.

The agent which selects for plants having an above-average amino acid content may also comprise lysine. Preferably, the lysine is present at a concentration ranging from 0.3 to 20 mM. More preferably, the lysine is present at a concentration ranging from 0.5 to 10 mM. Even more preferably, the lysine is present at a concentration ranging from 1.0 to 4.0 mM.

The present invention also comprises seeds derived from plant lines generated using the methods of the invention, wherein the seeds are capable of propagating the modified plant lines having the predetermined altered phenotype of interest.

In another aspect, the invention comprises a method for producing a modified tobacco line having an increased amount of at least one amino acid as compared to an unmodified parent tobacco line comprising the steps of: incubating tobacco seeds in a solution comprising a mutagen; washing the seeds free of the mutagen; germinating the seeds and growing M1 seedlings; adding a medium comprising threonine and lysine to the M1 seedlings; growing the M1 seedlings to generate at least one chimeric plant comprising M2 seeds, wherein the M2 seeds from the chimeric plant comprise non-mutagenized M2 seeds and mutagenized M2 seeds; and germinating the M2 seeds in medium comprising threonine and lysine to select for the modified lines. In an embodiment, the method includes growing the M2 tobacco plants to generate M3 seeds, wherein at least one of the M2 plants is a heterozygote and at least one of the M2 plants is a homozygote for a mutation conferring the ability to grow in the presence of increased threonine and lysine, and germinating the M3 seeds in medium comprising threonine and lysine to identify at least one homozygote M2 plant.

In an embodiment, the second medium comprising threonine and lysine is added to the M1 seedlings at certain developmental stages such as during a predetermined time period after germination. Preferably, the second medium comprising threonine and lysine is added to the M1 seedlings 7 to 14 days after germination. More preferably, the second medium comprising threonine and lysine is added to the M1 seedlings 10 days after germination. In an embodiment, the mutagenized seeds are suspended in nutrient medium and applied to a semi-permeable surface for growth on liquid medium prior to application of the selection agent.

Preferably, the tobacco line comprises the genus *Nicotiana*. More preferably, the tobacco line comprises the species *Nicotiana tobacum*.

In an embodiment, the mutagen is ethyl methanesulfonate (EMS). Preferably, the EMS is present at a final concentration of 0.01 to 2%. More preferably, the EMS is present at a final concentration of 0.05 to 1%. Even more preferably, the EMS is present at a final concentration of 0.1 to 0.3%.

Preferably, the threonine concentration ranges from 0.3 to 20 mM. More preferably, the threonine concentration ranges from 0.5 to 10 mM. Even more preferably, the threonine concentration ranges from 1.0 to 4.0 mM. Also preferably, the lysine concentration ranges from 0.3 to 20 mM. More preferably, the lysine concentration ranges from 0.5 to 10 mM. Even more preferably, the lysine concentration ranges from 1.0 to 4.0 mM.

In an embodiment, the modified tobacco line has at least a 2 fold increase in total amino acids. For example, in an embodiment, the modified tobacco lines comprise an increase in threonine content as compared to the unmodified parent. More preferably, the modified tobacco lines comprise at least a 2 to 150 fold increase in threonine. Even more preferably, the modified tobacco lines comprise at least a 5 to 150 fold increase in threonine. Even more preferably, the modified tobacco lines produce plants comprising at least a 150 fold increase in threonine.

In an embodiment, the modified tobacco line comprises an increase in the concentration of at least one of the following amino acids: threonine, asparagine, glutamine, glutamic acid, serine, aspartic acid, leucine, isoleucine, phenylalanine, lysine, arginine, histidine, tyrosine, or glycine. Preferably, the increase in at least one amino acid as compared to the unmodified parent tobacco line comprises at least a 2 fold increase. More preferably, the increase in at least one amino acid as compared to the unmodified parent tobacco line comprises at least a 5 fold increase. Even more preferably, the increase in at least one amino acid as compared to the unmodified parent tobacco line comprises at least a 10 fold increase. Even more preferably, the increase in at least one amino acid as compared to the unmodified parent tobacco line comprises at least a 100 fold increase.

Thus, the modified tobacco lines may comprise an increase in asparagine content as compared to the unmodified parent. Preferably, the modified tobacco lines comprise at least a 2 to 4 fold increase in asparagine. Alternatively, the modified tobacco lines may comprise an increase in glutamine content as compared to the unmodified parent. Preferably, the modified tobacco lines comprise at least a 2 to 5 fold increase in glutamine. In an embodiment, the modified tobacco lines comprise an increase in glutamic acid content as compared to the unmodified parent. Preferably, the modified tobacco lines comprise at least a 2 to 4 fold increase in glutamic acid. In yet another embodiment, the modified tobacco lines comprise an increase in serine content as compared to the unmodified parent. Preferably, the modified tobacco lines comprise at least a 2 fold increase in serine. In another embodiment, the modified tobacco lines may comprise an increase in aspartic acid content as compared to the unmodified parent. Preferably, the modified tobacco lines comprise at least a 2 fold increase in aspartic acid. In an embodiment, the modified tobacco lines comprise an increase in leucine content as compared to the unmodified parent. Preferably, the modified tobacco lines comprise at least a 2 fold increase in leucine. In another embodiment, the modified tobacco lines comprise an increase in isoleucine content as compared to the unmodified parent. Preferably, the modified tobacco lines comprise at least a 2 fold increase in isoleucine. The modified tobacco lines may also comprise an increase in phenylalanine content as compared to the unmodified parent. Preferably, the modified tobacco lines comprise at least a 2 to 4 fold increase in phenylalanine. In another embodiment, the modified tobacco lines comprise an increase in lysine content as compared to the unmodified parent. Preferably, the modified tobacco lines comprise at least a 2 to 3 fold increase in lysine. In an alternative embodiment, the modified tobacco lines comprise an increase in arginine content as compared to the unmodified parent. Preferably, the modified tobacco lines comprise at least a 2 to 7 fold increase in arginine. In an embodiment, the modified tobacco lines comprise an increase in histidine as compared to the unmodified parent. Preferably, the modified tobacco lines comprise at least a 2 to 4 fold increase in histidine. In an embodiment, the modified tobacco lines comprise an increase in tyrosine as compared to the unmodified parent. Preferably, the modified tobacco lines comprise at least a 2 fold increase in tyrosine. In yet another embodiment, the modified tobacco lines comprise an increase in glycine as compared to the unmodified parent. Preferably, the modified tobacco lines comprise at least a 2 fold increase in glycine.

The present invention also comprises seeds derived from plant lines generated using the methods of the invention, wherein the seeds are capable of propagating the modified plant lines having an above average content of at least one amino acid.

In one aspect, the present invention comprises a method for improving the flavor of tobacco product comprising generating a modified tobacco plant comprising an increase in the concentration of at least one amino acid, mixing the modified tobacco with unmodified tobacco, and including the mixture in a tobacco product. Preferably, the modified tobacco plant is made by mutagenizing tobacco seeds and selecting for partially mutagenized chimeric plants. Preferably, the amino acid comprising an increased concentration comprises at least one hydroxy amino acid. More preferably, the amino acid comprising an increased concentration is threonine.

In another aspect, the present invention comprises a modified tobacco plant having an above-average amount of at least one amino acid as compared to an unmodified parent tobacco line, wherein the genome of the modified tobacco plant consists essentially of plant DNA. Preferably, the genome of the modified tobacco plant consists essentially of tobacco DNA. Even more preferably, the aspartate kinase genes of the modified tobacco plant consist essentially of tobacco genomic DNA. Preferably, the tobacco plant comprises the genus *Nicotiana*. More preferably, the modified tobacco plant comprises the species *Nicotiana tobacum*.

In an embodiment, the modified tobacco plant comprises at least a 2 fold increase in total amino acids. In an embodiment, the modified tobacco plant comprises an increase in threonine. Preferably, the modified tobacco plant comprises at least a 2 to 150 fold increase in threonine. More preferably, the modified tobacco plant comprises at least a 5 to 150 fold increase in threonine. Even more preferably, the modified tobacco plant comprises at least a 150 fold increase in threonine.

In an embodiment, the modified plant comprises an increase of at least one of the following amino acids: threonine, asparagine, glutamine, glutamic acid, serine, aspartic acid, leucine, isoleucine, phenylalanine, lysine, arginine, histidine, tyrosine, or glycine. Preferably, the increase in at least one amino acid as compared to the unmodified parent tobacco line comprises at least a 2 fold increase. More preferably, the increase in at least one amino acid as compared to the unmodified parent tobacco line comprises at least a 5 fold increase. Even more preferably, the increase in at least one amino acid as compared to the unmodified parent tobacco line comprises at least a 10 fold increase. Even more preferably, the increase in at least one amino acid as compared to the unmodified parent tobacco line comprises at least a 100 fold increase.

The present invention also includes a modified tobacco plant having an above-average amount of at least one amino acid as compared to an unmodified parent tobacco line, wherein the modified plant has essentially the same antibiotic resistance as the unmodified parent line. Preferably, the tobacco plant comprises the genus *Nicotiana*. More preferably, the modified tobacco plant comprises the species *Nicotiana tobacum*.

Preferably, the modified tobacco plant has at least a 2 fold increase in total amino acids. Preferably, the modified tobacco plant comprises an increase in threonine. Preferably, the modified tobacco plant comprises at least a 2 to 150 fold increase in threonine. More preferably, the modified tobacco plant comprises at least a 5 to 150 fold increase in threonine. Even more preferably, the modified tobacco plant comprises at least a 150 fold increase in threonine. The modified plant may also comprise an increase of at least one of the following amino acids: threonine, asparagine, glutamine, glutamic acid, serine, aspartic acid, leucine, isoleucine, phenylalanine, lysine, arginine, histidine, tyrosine, or glycine. Preferably, the increase in any one amino acid is at least 2 fold, more preferably, at least 5 fold, even more preferably, at least 10 fold, and even more preferably, the increase an any one or more amino acid is at least 100 fold Also, the present invention comprises a modified tobacco plant having an above-average amount of at least one amino acid as compared to an unmodified parent tobacco line, wherein the aspartate kinase genes of the modified tobacco plant comprise plant DNA. More preferably, the aspartate kinase genes of the modified tobacco plant comprise tobacco genomic DNA. Also preferably, the tobacco plant comprises the genus *Nicotiana*. More preferably, the modified tobacco plant comprises the species *Nicotiana tobacum*. Also, the present invention comprises seeds capable of propagating the modified plant lines having an above-average content of at least one amino acid.

In an embodiment, the modified tobacco plant comprises at least a 2 fold increase in total amino acids. In an embodiment, the modified tobacco plant comprises an increase in threonine as compared to an unmodified parent tobacco line. Preferably, the modified tobacco plant comprises at least a 2 to 150 fold increase in threonine. More preferably, the modified tobacco plant comprises at least a 5 to 150 fold increase in threonine. Even more preferably, the modified tobacco plant comprises at least a 150 fold increase in threonine. The modified plant may also comprise an increase, as compared to the unmodified parent tobacco line, in the concentration of at least one of the following amino acids: threonine, asparagine, glutamine, glutamic acid, serine, aspartic acid, leucine, isoleucine, phenylalanine, lysine, arginine, histidine, tyrosine, or glycine. Preferably, the increase in any one amino acid is at least 2 fold, more preferably, at least 5 fold, even more preferably, at least 10 fold, and even more preferably, the increase in any one or more amino acid is at least 100 fold.

In another aspect, the present invention comprises a modified tobacco plant having an above-average amount of at least one amino acid as compared to an unmodified parent tobacco line, wherein the tobacco plant is produced by mutagenesis of tobacco genomic DNA and selection of M1 plants having a mutation of interest. Preferably, the tobacco plant is produced by the steps of: mutagenizing tobacco seeds; germinating the mutagenized seeds and growing M1 seedlings; adding medium comprising threonine and lysine to the seedlings; growing at least one chimeric M1 plant to generate M2 seeds, wherein the M2 seeds from the chimeric plant comprise non-mutagenized M2 seeds and mutagenized M2 seeds; and germinating the M2 seeds in medium containing threonine and lysine to select for mutagenized M2 plants. More preferably, the method of preparing the modified plant includes the steps of growing the M2 tobacco plants to generate M3 seeds, wherein at least one of the M2 plants is a heterozygote and at least one of the M2 plants is a homozygote for a mutation conferring the ability to grow in the presence of increased threonine and lysine; and germinating the M3 seeds in medium comprising threonine and lysine to identify at least one homozygote M2 plant. The tobacco plant preferably comprises the genus *Nicotiana*, and even more preferably, the species *Nicotiana tobacum*.

In an embodiment, the modified tobacco plant produced by mutagenesis of tobacco DNA comprises at least a 2 fold increase in total amino acids. In an embodiment, the modified tobacco plant comprises an increase in threonine as compared to an unmodified parent tobacco line. Preferably, the modified tobacco plant comprises at least a 2 to 150 fold increase in threonine. More preferably, the modified tobacco plant comprises at least a 5 to 150 fold increase in threonine. Even more preferably, the modified tobacco plant comprises at least a 150 fold increase in threonine. The modified plant may also comprise an increase, as compared to the unmodified parent tobacco line, in the concentration of at least one of the following amino acids: threonine, asparagine, glutamine, glutamic acid, serine, aspartic acid, leucine, isoleucine, phenylalanine, lysine, arginine, histidine, tyrosine, or glycine. Preferably, the increase in any one amino acid is at least 2 fold, more preferably, at least 5 fold, even more preferably, at least 10 fold, and even more preferably, the increase in any one or more amino acid is at least 100 fold.

Thus, in an embodiment, the modified tobacco plants comprise an increase in asparagine content as compared to the unmodified parent tobacco line. Preferably, the modified tobacco plants comprise at least a 2 to 4 fold increase in asparagine. Alternatively, the modified tobacco plants may comprise an increase in glutamine content as compared to the unmodified parent tobacco line. Preferably, the modified tobacco plants comprise at least a 2 to 5 fold increase in glutamine. In an embodiment, the modified tobacco plants comprise an increase in glutamic acid content as compared to the unmodified parent tobacco line. Preferably, the modified tobacco plants comprise at least a 2 to 4 fold increase in glutamic acid. In an embodiment, the modified tobacco plants comprise an increase in serine content as compared to the unmodified parent tobacco line. Preferably, the modified tobacco plants comprise at least a 2 fold increase in serine as compared to the unmodified parent tobacco line. In another embodiment, the modified tobacco plants comprise an increase in aspartic acid content as compared to the unmodified parent tobacco line. Preferably, the modified tobacco plants comprise at least a 2 fold increase in aspartic acid. The modified tobacco plants may comprise an increase in leucine content as compared to the unmodified parent tobacco line. Preferably, the modified tobacco plants comprise at least a 2 fold increase in leucine. In another embodiment, the modified tobacco plants comprise an increase in isoleucine content as compared to the unmodified parent tobacco line. Preferably, the modified tobacco plants comprise at least a 2 fold increase in isoleucine. In another embodiment, the modified tobacco plants comprise an increase in phenylalanine content as compared to the unmodified parent tobacco line. Preferably, the modified tobacco plants comprise at least a 2 to 4 fold increase in phenylalanine. The modified tobacco plants may comprise an increase in lysine content as compared to the unmodified parent tobacco line. Preferably, the modified tobacco plants comprise at least a 2 to 3 fold increase in lysine. In an embodiment, the modified tobacco plants comprise an increase in arginine content as compared to the unmodified parent tobacco line. Preferably, the modified tobacco plants comprise at least a 2 to 7 fold increase in arginine. In an embodiment, the modified tobacco plants comprise an increase in histidine as compared to the unmodified parent tobacco line. Preferably, the modified tobacco plants comprise at least a 2 to 4 fold increase in histidine. In another embodiment, the modified tobacco plants comprise an increase in tyrosine as compared to the unmodified parent tobacco line. Preferably, the modified tobacco plants comprise at least a 2 fold increase in tyrosine. In yet another embodiment, the modified tobacco plants comprise an increase in glycine as compared to the unmodified parent tobacco line. Preferably, the modified tobacco plants comprise at least a 2 fold increase in glycine. Also, the present invention comprises seeds capable of propagating the modified plants having an above-average content of at least one amino acid.

In another aspect, the present invention comprises a composition comprising a modified tobacco plant having an above-average amount of at least one amino acid as compared to an unmodified parent tobacco line, wherein the genome of the modified tobacco plant comprises plant DNA, or wherein the modified tobacco plant is produced by mutagenesis of tobacco genomic DNA and selection of M1 plants having a mutation of interest.

Preferably, the modified tobacco plant comprises the genus *Nicotiana*. More preferably, the modified tobacco plant comprises the species *Nicotiana tobacum*.

Preferably, the composition comprises a modified tobacco plant having at least a 2 fold increase in total amino acid concentration. In an embodiment, the modified tobacco plant comprises an increase in threonine. Preferably, the modified tobacco plant comprises at least a 2 to 150 fold increase in threonine. More preferably, the modified tobacco plant comprises at least a 5 to 150 fold increase in threonine. Even more preferably, the modified tobacco plant comprises at least a 150 fold increase in threonine.

In an embodiment, the modified plant comprises an increase of at least one of the following amino acids: threonine, asparagine, glutamine, glutamic acid, serine, aspartic acid, leucine, isoleucine, phenylalanine, lysine, arginine, histidine, tyrosine, or glycine. Preferably, the increase in at least one amino acid as compared to the unmodified parent tobacco line comprises at least a 2 fold increase. More preferably, the increase in at least one amino acid as compared to the unmodified parent tobacco line comprises at least a 5 fold increase. Even more preferably, the increase in at least one amino acid as compared to the unmodified parent tobacco line comprises at least a 10 fold increase. Even more preferably, the increase in at least one amino acid as compared to the unmodified parent tobacco line comprises at least a 100 fold increase.

The present invention also comprises an article of manufacture comprising a modified tobacco plant having an above-average amount of at least one amino acid as compared to an unmodified parent tobacco line, wherein the genome of the modified tobacco plant comprises plant DNA or wherein the modified tobacco plant is produced by mutagenesis of tobacco genomic DNA and selection of M1 plants having a mutation of interest.

Preferably, the modified tobacco plant comprises the genus *Nicotiana*. More preferably, the modified tobacco plant comprises the species *Nicotiana tobacum*.

Preferably, the article of manufacture comprises modified tobacco plant having at least a 2 fold increase in total amino acid concentration as compared to the unmodified parent line. In an embodiment, the modified tobacco plant comprises an increase in threonine. Preferably, the modified tobacco plant comprises at least a 2 to 150 fold increase in threonine. More preferably, the modified tobacco plant comprises at least a 5 to 150 fold increase in threonine. Even more preferably, the modified tobacco plant comprises at least a 150 fold increase in threonine.

The modified plant preferably comprises an increase of at least one of the following amino acids: threonine, asparagine, glutamine, glutamic acid, serine, aspartic acid, leucine, isoleucine, phenylalanine, lysine, arginine, histidine, tyrosine, or glycine. In an embodiment, the increase in at least one amino acid as compared to the unmodified parent tobacco line comprises at least a 2 fold increase. More preferably, the increase in at least one amino acid as compared to the unmodified parent tobacco line comprises at least a 5 fold increase. Even more preferably, the increase in at least one amino acid as compared to the unmodified parent tobacco line comprises at least a 10 fold increase. Even more preferably, the increase in at least one amino acid as compared to the unmodified parent tobacco line comprises at least a 100 fold increase.

In yet another aspect, the present invention comprises a seed capable of propagating a modified tobacco plant comprising an above-average amount of at least one amino acid as compared to the parent line from which the modified plant is derived.

Thus, the present invention relates to a novel method for producing plants with an altered phenotype by selection at the M1 chimeric stage. Mutagenesis has been used as a conventional breeding method to develop improved cultivars of a number crops, including tobacco (see e.g. A. M. van Harten, *Mutation Breeding: Theory and Practical Appli-* *cations*, pp. 1–63, Cambridge Univ. Press, New York, N.Y., 1998). Generally, the target plant materials used to develop desired mutant using chemical mutagens are classified into two categories: (1) seed, and (2) tissue or cell culture. In light of the desirability of increasing amino acid production in plants, selection of plants resistant to high levels of lysine plus threonine after mutagenesis has been employed to elevate the concentration of threonine in barley (Bright, S. W. J., et al., 1982a, *Nature* 299: 278–270; Bright S. W. J., et al., 1982b, *Biochem. Genet.*, 20: 229–243), carrot (Cattoir-Reynaerts, A., et al., 1983, *Biochem. Physiol. Pflanz* 178: 89–90), maize (Diedrick, T. J., et al., 1990, *Theor. Appl. Genet.*, 79: 209–215; Dotson, S. B. et al., 1990, *Planta* 182: 546–552; Hibberd et al., 1980, *Planta* 148: 183–187), and *Arabidopsis thaliana* (B. Heremans and M. Jacobs, 1995, *J. Plant Physiol.*, 146: 249–257).

For example, seeds may be treated with specific mutagens, and the surviving seeds grown to produce their progenies (e.g. Heremans and Jacobs, 1995). The generation that grows from the mutagenized seed is called the M1 generation, and the progeny collected from the M1 plants are the M2 generation, from which the desired mutants are usually selected. Further selection of plants which are homozygous for the mutation of interest may be made by growing progeny from M2 plants (i.e. the M3 generation) under selective conditions. It has been estimated that an M1 population size of about 125,000 plants is needed to saturate the genome for all possible mutations induced by the chemical mutagen ethyl methane sulfonate (EMS) in *Arabidopsis thaliana* (G. W. Haughn and C. R. Somerville, 1987, *Selection for Herbicide Resistance at the Whole Plant Level*, In: Biotechnology in Agricultural Chemistry, H. M. Lebaron et al., eds., American Chemical Society, Washington, D.C., pp. 98–108). Since the genome of *Nicotiana tobacum* is about 38 times as large as that of *Arabidopsis*, a M1 population of approximately 4,750,000 plants is needed to saturate the tobacco genome for all possible EMS-induced mutations, which would then be grown for selection as the M2 generation. Due to their size and cultivation requirements, it is generally not practical to grow this of a large population of M1 plants for creating mutants of interest in tobacco.

Although mutagenesis and selection is much easier to perform on tissue culture cells (e.g. Cattoir-Reynaerts et al., 1983; Dotson et al., 1990; Hibberd et al., 1980), the mutant cells or tissues must be regenerated to fertile plants. Establishment of a system for regeneration of a fertile plant from the genotype of interest is time-consuming, expensive, and requires a high level of technical expertise. In addition, undesired somaclonal variation often occurs in regenerated mutants of interest as a result of autosomal chromosome duplications. This approach has been used with some success for *N. sylvestris*, a diploid non-commercial strain of tobacco (Frankard, V., et al., 1991, *Theor. Appl. Genet.*, 82: 273–282; Frankard, V., et al., 1992, *Plant Physiol.*, 99:1285–93), and other plants. Still, it is not clear whether this approach is practical for alloploid genomes found in many commercial crops (e.g., tobacco, wheat, and cotton).

Genetic engineering has also been used produce transgenic plants which overproduce threonine. Although the tobacco AK gene has not been characterized, expression of a bacterial AK results in overproduction of free threonine in *N. tobacum* (O. Shaul and G. Galili, 1992, *Plant Physiol.*, 100:1157–1163; Karchi, H., et al., 1993, *Plant J.*, 3: 721–727), canola, soybean and maize (Falco, S. C., et al., 1995, *Biotechnology* 13: 577–582; Falco, S. C., et al., 1997, *SIM News* 47: 53–57). Still, this approach is technically demanding, requires introduction of foreign DNA into the genome, and does not generate the wide variety of mutants needed for propagation of a crop in various ecosystems. In addition, the effects of transgenic crops produced by genetic engineering on the long-term stability of ecosystems is not known (N. C. Ellstrand, 2001, *Plant Physiol.*, 125: 1543–1545). Finally, transgenic crops have not been widely accepted by the public, especially in European countries.

Figure 2:
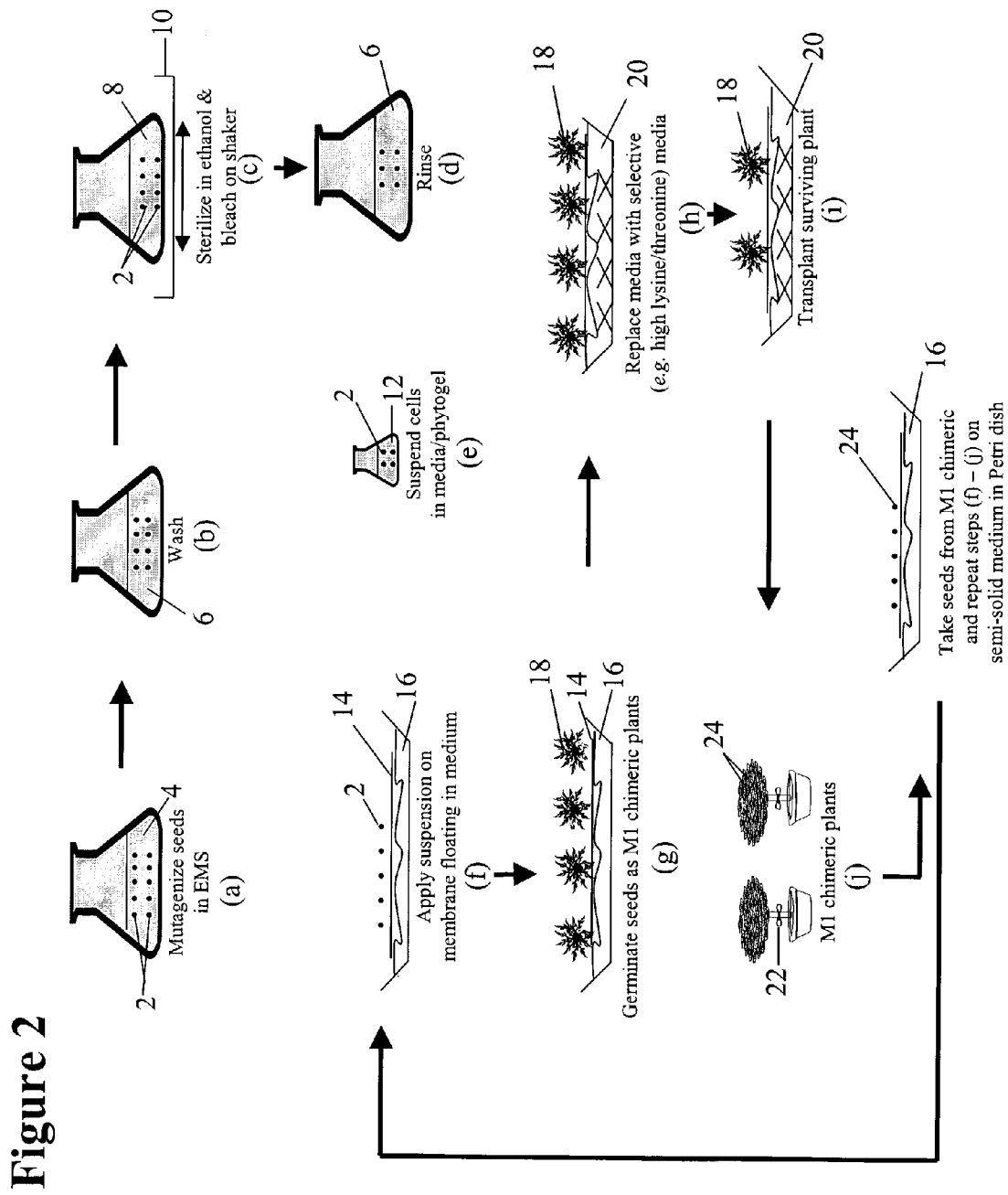
FIG. 2 is a schematic representation illustrating an aspect of an embodiment of the method of the present invention.

It is therefore an object of the present invention to develop a new method whereby the screening is at least in part performed using M1 plants. To screen the M1 generation, the trait of interest is preferably controlled by dominant or semi-dominant alleles. For example, an M1 generation of *Arabidopsis* having an gai/gai genotype (dwarfed phenotype) and irradiated with γ rays, can be grown under normal conditions for selection of heterozygous revertants (GAI/gai) having only a partially stunted phenotype (J. Peng and N. P. Harberd, 1993, *The Plant Cell* 5: 351–360). Referring now to FIG. 2, in one aspect, the invention provides a method of producing *Nicotiana tobacum* lines having above average amino acid content. In an embodiment, the method comprises the steps of: (a) mutagenizing seeds 2 of *N. tobacum* in a solution containing the mutagen ethyl methane-sulfonate (EMS) 4 at a concentration of about 0.1–0.3% for 20 hrs; (b) washing the mutagenized seeds in water 6; (c) sterilizing the seeds 2 with 70% ethanol followed by 20% Chlorox bleach 8 on an agitating shaker 10; (d) rinsing with sterile water 6; (e) suspending the seeds 2 in nutrient medium with 0.1% Phytagel (a semi-solid colloidal suspension) 12; (f) applying about 0.5 ml of the suspension with about 200 seeds 2 onto a floating membrane 14 suspended in growth medium 16; (g) germinating the seeds and growing the seedlings 18 in a tissue culture room at 25° C. with a 16-h photoperiod from cool-white fluorescent lamps; (h) after 7 to 14 days, replacing the growth medium 16 with medium containing threonine and lysine 20 to select for plants having resistance to feedback inhibition of methionine biosynthesis; (i) transplanting the surviving seedlings 18 in soil and growing as plants 22 in a greenhouse; and (j) planting individual seeds 24 from M1 chimeric plants in selective conditions (high levels of serine and threonine) for selection of pure (i.e. non-chimeric) M2 *N. tobacum* lines producing higher than average levels of threonine (i.e. repeating steps (f) through (j)). These non-chimeric tobacco plants are a mixture of hetergzygotes and homozygotes. An additional selection step may therefore be added for selection of tobacco lines which are homozygous for resistance to increased threonine and/or lysine.

As defined herein, media comprises compositions which are suited for maintenance or growth of biological tissue. Media may comprise water, buffered solutions, soil, or a growth medium, such as, but not limited to, the media described in the examples herein. Generally, any composition which is biologically compatible with the plant of interest is suitable.

Also as defined herein, mutagenesis comprises a process that results in a modification of a DNA sequence. Mutagenesis may include transitions, transversions, base additions or deletions causing frameshifts, or crosslinking of nucleotides, as well as modification/substitution of bases such that binding of proteins to DNA (e.g. transcription factors) is altered. Also included are methods comprising genetic engineering such as site-directed mutagenesis.

The plants included in the present invention also include plants which may be genetically engineered using non-tobacco DNA at a locus distinct from the aspartate kinase genes. For example, plants which are genetically engineered to be resistant to pesticides and which are also modified by mutagenesis of tobacco genomic DNA at the aspartate kinase loci to become high amino acid producers are included in the present invention. In one embodiment, the plants of the present invention comprise plants having essentially the same antibiotic resistance profile as the unmodified plant parent line, such that the modified plants do not comprise a novel antibiotic resistance as compared to the unmodified parent line.

A mutagen is defined as a substance (or treatment) which can change (mutate) the DNA in a cell. Typical chemical mutagens include, but are not limited to, ethyl methanesulfonate (EMS), nitrous acid, 5-bromouracil, methyl-nitrosoguanidine, and frameshift mutagens such as proflavin and the like. Mutations can also be generated by radiation, such as UV, X-rays, γ-rays, and the like. Mutagens also include agents such as viral vectors, transponsons, and the like, which can facilitate the insertion of foreign DNA into the tobacco genome.

Generally, the first generation treated with a mutagen comprises the M1 generation. Subsequent generations are then described as M2 (one generation after the mutagenesis event), M3 (two generations after the mutagenesis event), and the like.

As defined herein, the physical appearance of an organism comprises its phenotype, whereas the genetic composition of an organism comprises its genotype. Heterozygotes are defined as genomes which carry a single mutation at a locus of interest. Thus, heterozygotes have two distinct alleles for a gene, each of which can be passed to the next generation. Homozygotes are defined as organisms having identical alleles at one or more loci. Thus, homozygotes carry the same alleles (e.g. two mutations or two normal sequences) at a locus of interest and, therefore, identical alleles will be passed to all progeny.

In one embodiment, the present invention provides lines of the species of *N. tobacum* that produce unusually high level of free amino acids. Specifically, these novel lines produce at least 120 nmoles of total amino acids per milligram dry weight in cured leaf. This represents at least a 2 fold increase in total free amino acid production over unmodified flue-cured *N. tobacum* parent, which normally yields a maximum of about 50–60 nmoles/mg.

In another embodiment, the present invention provides novel lines of *N. tobacum* that produce unusually high levels of individual amino acid in flue-cured tobacco leaves. Preferably, these novel plant lines produce at least 0.5 nmoles of free threonine per milligram of dry leaf weight, more preferably at least 0.7 nmole/mg free threonine per milligram of dry leaf weight, and even more preferably at least 1.3 nmole/mg free threonine per milligram of dry leaf weight of flue-cured leaf material. This represents a 3 to 6 fold increase in free threonine production over the unmodified *N. tobacum* parent line, which normally produces 0.22 nmoles of free threonine per milligram of dry leaf weight of flue-cured leaf material.

The amount of a specific amino acid may be dependent on processing of the leaf, or the developmental stage of the plant. In an embodiment, the relative increases in amino acid values are higher in flue cured material than in green leaves from the same line. Still, tobacco lines comprising increased amino acids in green leaves are produced by the methods of the invention. For example, in an embodiment, cell lines comprising at least 15.8 and 20.1 nmole/mg green leaf weight, or a 6 to almost 8 fold increase in threonine over the unmodified *N. tobacum* parent line are produced. In yet another embodiment, plants have a greater than 150 fold increase in free threonine, but are sterile.

In an embodiment, the present invention provides novel lines of *N. tobacum* that produce unusually high levels of asparagine in flue-cured tobacco leaves. Preferably, these novel plant lines produce at least 29.6 nmoles of free asparagine per milligram of dry leaf weight of flue-cured leaf material, more preferably at least 37.4 nmole of free asparagine per milligram of dry leaf weight, and even more preferably at least 38.4 nmole of free asparagine per milligram of dry leaf weight. This represents a 3 to 4 fold increase in free asparagine production over unmodified *N. tobacum* parent line, which normally produces about 8.22 nmoles of free asparagine per milligram of dry leaf weight of flue-cured leaf material.

The present invention also provides novel lines of *N. tobacum* that produce unusually high levels of glutamine in flue-cured tobacco leaves. Preferably, these novel plant lines produce 24.7 nmoles of free glutamine per milligram of dry leaf weight of flue-cured leaf material, more preferably at least 28.3 nmole of free glutamine per milligram of dry leaf weight, and even more preferably at least about 37.3 nmole of free glutamine per milligram of dry leaf weight. This represents a 3 to 5 fold increase in free glutamine production over unmodified *N. tobacum* parent line, which normally produces about 6.68 nmoles of free glutamine per milligram of dry leaf weight of flue-cured leaf material.

In another embodiment, the present invention provides novel lines of *N. tobacum* that produce unusually high levels of glutamic acid in flue-cured tobacco leaves. Preferably, these novel plant lines produced 1.50 nmoles of free glutamic acid per milligram of dry leaf weight of flue-cured leaf material, more preferably at least 1.56 nmole of free glutamic acid per milligram of dry leaf weight, and even more preferably at least about 2.23 nmole of free glutamic acid per milligram of dry leaf weight. This represents about a 3 to 4 fold increase in free glutamic acid production over unmodified *N. tobacum* parent line, which normally produces about 0.53 nmoles of free glutamic acid per milligram of dry leaf weight of flue-cured leaf material.

The present invention also provides novel lines of *N. tobacum* that produce unusually high levels of serine in flue-cured tobacco leaves. Preferably, these novel plant lines produced at least 1.15 nmoles of free serine per milligram of dry leaf weight of flue-cured leaf material, more preferably at least 1.41 nmole of free serine per milligram of dry leaf weight, and even more preferably at least 1.72 nmole of free serine per milligram of dry leaf weight. This represents a 79% to 168% increase in free serine production over unmodified *N. tobacum* parent line, which normally produces about 0.64 nmoles of free serine per milligram of dry leaf weight of flue-cured leaf material.

In another embodiment, the present invention provides novel lines of *N. tobacum* that produce unusually high levels of aspartic acid in flue-cured tobacco leaves. Preferably, these novel plant lines produce at least 2.5 nmoles of free aspartic acid per milligram of dry leaf weight of flue-cured leaf material, more preferably at least 3.2 nmole of free aspartic acid per milligram of dry leaf weight, and even more preferably at least 4.2 nmole of free aspartic acid per milligram of dry leaf weight. This represents a 72% to 184% increase in free aspartic acid production over unmodified *N. tobacum* parent line, which normally produces about 1.48 nmoles of free aspartic acid per milligram of dry leaf weight of flue-cured leaf material.

The present invention also provides novel lines of *N. tobacum* that produce unusually high levels of leucine in flue-cured tobacco leaves. Preferably, these novel plant lines produce preferably at least 0.16 nmoles of free leucine per milligram of dry leaf weight of flue-cured leaf material, and more preferably at least about 0.19 nmole of free leucine per milligram of dry leaf weight. This represents a 75% to 113% increase in free leucine production over unmodified *N. tobacum* parent line, which normally produces about 0.09 nmoles of free leucine per milligram of dry leaf weight of flue-cured leaf material.

In another embodiment, the present invention provides novel lines of *N. tobacum* that produce unusually high levels of isoleucine in flue-cured tobacco leaves. Preferably, these novel plant lines produce 0.06 nmoles of free isoleucine per milligram of dry leaf weight of flue-cured leaf material, more preferably at least 0.08 nmole of free isoleucine per milligram of dry leaf weight, and even more preferably at least about 0.1 nmole of free isoleucine per milligram of dry leaf weight. In a preferred embodiment, this represents a 45% to 136% increase in free isoleucine production over unmodified *N. tobacum* parent line, which normally produces about 0.04 nmoles of free isoleucine per milligram of dry leaf weight of flue-cured leaf material.

The present invention also provides novel lines of *N. tobacum* that produce unusually high levels of phenylalanine in flue-cured tobacco leaves. Preferably, these novel plant lines produce 0.51 nmoles of free phenylalanine per milligram of dry leaf weight of flue-cured leaf material, more preferably at least 0.75 nmoles of free phenylalanine per milligram of dry leaf weight, and even more preferably at least about 0.92 nmoles of free phenylalanine per milligram of dry leaf weight. This represents a 2 to 4 fold increase in free phenylalanine production over unmodified *N. tobacum* parent line, which normally produces about 0.20 nmoles of free phenylalanine per milligram of dry leaf weight of flue-cured leaf material.

In another embodiment, the present invention provides novel lines of *N. tobacum* that produce unusually high levels of lysine in flue-cured tobacco leaves. Preferably, these novel plant lines produce 0.33 nmoles of free lysine per milligram of dry leaf weight of flue-cured leaf material, more preferably at least 0.42 nmoles of free lysine per milligram of dry leaf weight, and even more preferably at least about 0.48 nmoles of free lysine per milligram of dry leaf weight. This represents a 2 to 3 fold increase in free lysine production over unmodified *N. tobacum* parent line, which normally produces about 0.14 nmoles of free lysine per milligram of dry leaf weight of flue-cured leaf material.

In another embodiment, the present invention provides novel lines of *N. tobacum* that produce unusually high levels of arginine in flue-cured tobacco leaves. Preferably, these novel plant lines produce at least 0.12 nmoles of free asparagine per milligram of dry leaf weight of flue-cured leaf material, and more preferably at least 0.26 nmole of free asparagine per milligram of dry leaf weight. This represents a 3 to 7 fold increase in free arginine production over unmodified *N. tobacum* parent line, which normally produces about 0.03 nmoles of free arginine per milligram of dry leaf weight of flue-cured leaf material.

The present invention also provides novel lines of *N. tobacum* that produce unusually high levels of histidine in flue-cured tobacco leaves. Preferably, these novel plant lines produce at least 1.55 nmoles of free histidine per milligram of dry leaf weight of flue-cured leaf material, more preferably at least 1.6 nmole of free histidine per milligram of dry leaf weight, and even more preferably at least 2.2 nmole of free histidine per milligram of dry leaf weight. This represents a 3 to almost 5 fold increase in free histidine production over unmodified *N. tobacum* parent line, which normally produces about 0.46 nmoles of free histidine per milligram of dry leaf weight of flue-cured leaf material.

In another embodiment, the present invention provides novel lines of *N. tobacum* that produce unusually high levels of tyrosine in flue-cured tobacco leaves. Preferably, these novel plant lines produce at least 0.25 nmoles of free tyrosine per milligram of dry leaf weight of flue-cured leaf material, and more preferably at least 0.45 nmole of free tyrosine per milligram of dry leaf weight. This represents 39 to 145% increase in free tyrosine production over unmodified *N. tobacum* parent line, which normally produces about 0.18 nmoles of free tyrosine per milligram of dry leaf weight of flue-cured leaf material.

In yet another embodiment, the present invention provides novel lines of *N. tobacum* that produce unusually high levels of glycine in flue-cured tobacco leaves. Preferably, these novel plant lines produce at least 0.44 nmoles of free glycine per milligram of dry leaf weight of flue-cured leaf material, more preferably at least 0.48 nmole of free glycine per milligram of dry leaf weight, and even more preferably at least 0.51 nmole of free glycine per milligram of dry leaf weight. This represents a 74 to 100% increase in free glycine production over unmodified *N. tobacum* parent line, which normally produces about 0.25 nmoles of free arginine per milligram of dry leaf weight of flue-cured leaf material.

These modified lines also provide the basis for the production of hybrid lines, utilizing as one or both parents, the novel lines of the present invention. Also within the scope of the present invention are clones, somaclones, and derivatives of the novel lines.

These modified lines further provide the basis for the production of a tobacco with specific amino acid precursor profiles useful for generating specific flavor compounds, including various pyrazines in roasted tobacco. For example, the present invention provides a method for improving the flavor of tobacco comprising generating a modified tobacco plant comprising an increase in threonine and mixing the modified tobacco with unmodified tobacco. The present invention may be better understood by reference to the following non-limiting examples.

EXAMPLE 1

The present invention has been used to prepare several lines of *N. tobacum* having above-average total free amino acid in flue cured lines. The mutagenized lines of *N. tobacum* have increased levels of most free amino acids, including threonine. Other amino acids increased more than 2 fold are asparagine, glutamic acid, glutamine, phenylalanine, lysine, histidine, and arginine. In addition, above-average levels of aspartic acid, serine, proline, glycine, alanine, methionine, isoleucine, leucine, and tyrosine are found in most of the modified lines.

To generate tobacco having increased amino acid concentration, seeds of *N. tobacum* were incubated in a solution containing ethyl methane sulfonate (EMS) at a concentration of about 0.1 to 0.3% for 20 hrs. The treated seeds were then washed with MiliQ water (purified with an NANO pure II system; Bamstead/Thermolyne Corp.; Dubuque, Iowa) for 30 minutes and sterilized with 70% ethanol for 30 seconds followed by 20% Clorox for 20 min on an agitating shaker.

After rinsing with sterile MiliQ water at least 5 times, the seeds were suspended in MSS nutrient medium (Table 1) containing 0.1% Phytagel (Sigma Chemical Co., St. Louis, Mo., USA). About 0.5 ml of the suspension (about 400 seeds/ml) was applied onto the membrane of a LifeRaft Float Unit in a Magenta Vessel (Life Technologies, Rockville, Md., USA) containing 0.5×MSS or 0.5×MS (0.5×MSS plus 1.5% sucrose) medium. The seeds were allowed to germinate in a tissue culture room at 25° C. with a 16-h photoperiod using cool-white fluorescent lamps (Sylvania, Danvers, Mass.) with an intensity of approximately 80 µE $m^{-2}$ $s^{-1}$. After 10 days, the growth medium was removed and the same medium containing threonine and lysine, each at a concentration of 1 to 4 mM, was added to the seedlings. The surviving plants were then transplanted into soil and grown in a greenhouse for development of *N. tobacum* lines resistant to high levels of threonine and lysine.

TABLE 1

| Murashige and Skoog Salt (MSS) | |
|---|---|
| COMPONENTS | Molarity (mM) |
| Ammonium Nitrate ($NH_4NO_3$) | 20.625 |
| Boric Acid ($H_3BO_3$) | 0.1 |
| Calcium Chloride ($CaCl_2$) (Anhyd.) | 3 |
| Cobalt Chloride ($CoCl_2$—$6H_2O$) | 0.0001 |
| Cupric Sulfate ($CuSO_4$—$6H_2O$) | 0.0001 |
| Ferric Sulfate ($FeSO_4$—$7H_2O$) | 0.1 |
| Magnesium Sulfate ($MgSO_4$) | 1.5 |
| Manganese Sulfate ($MnSO_4$—$H_2O$) | 0.1 |
| Potassium Iodide (KI) | 0.005 |
| Potassium Nitrate ($KNO_3$) | 18.81 |
| Potassium Phosphate ($KH_2PO_4$) | 1.25 |
| Sodium Molybdate ($Na_2MoO_4$—$2H_2O$) | 0.001 |
| Zinc Sulfate ($ZnSO4$—$7H2O$) | 0.03 |
| Glycine (Free Base) | 0.026 |
| Sodium EDTA ($Na_2$-EDTA) | 0.1 |
| myo-Inositol | 0.5556 |
| Nicotine Acid | 0.0004 |
| Pyridoxine HCl | 0.0002 |
| Thiamine HCl | 0.0003 |

Figure 3:
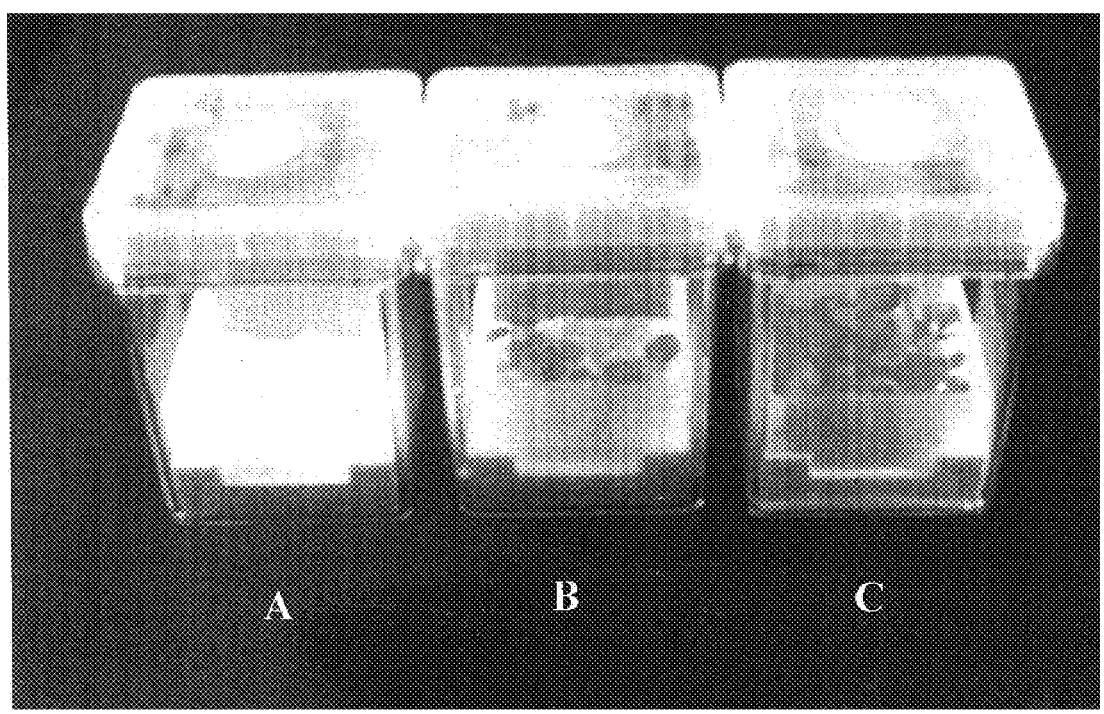
FIG. 3 illustrates an aspect of an embodiment of the method of the present invention comprising N. tobacum seedlings growing in Magenta Vessels containing 0.5×MS nutrient medium in the first screening, wherein (A) shows non-mutagenized seedlings that died in medium containing 2 mM lysine and 2 mM threonine, (B) shows seedlings from EMS-treated seeds growing in medium containing 2 mM lysine and 2 mM threonine, and (C) shows the seedlings from EMS-treated seeds growing in medium without lysine and threonine.

FIG. 3 shows M1 *N. tobacum* seedlings growing in Magenta Vessels containing 0.5×MS nutrient medium in the first screening (i.e. medium+lysine and threonine) after about 4 weeks. It can be seen (FIG. 3A) that seeds which were not treated with EMS (i.e. non-mutagenized) are unable to survive in a Magenta Vessel containing 2 mM lysine and 2 mM threonine, presumably due to feedback inhibition of methionine synthesis caused by exogenous lysine and threonine. At least some of the EMS-treated seeds, however, are able to grow in medium containing 2 mM lysine and 2 mM threonine, apparently due to mutagenesis of enzyme(s) required for feedback inhibition by threonine or lysine. As expected, a greater percentage of EMS-treated seeds incubated in medium without lysine and threonine are able to grow (FIG. 3C).

Figure 4:
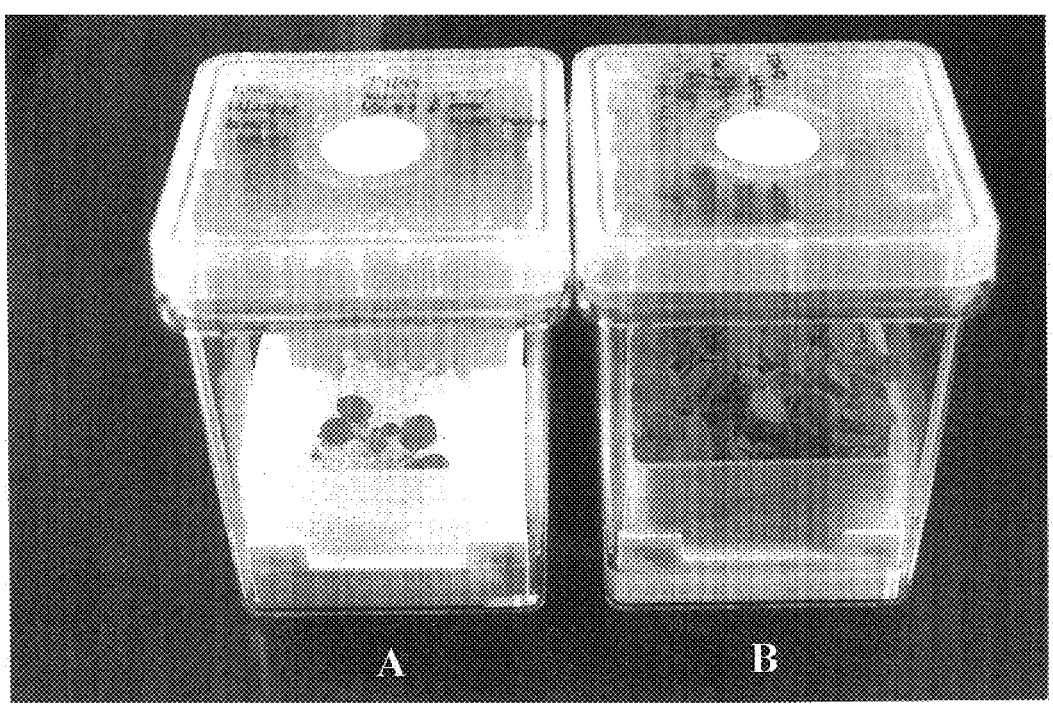
FIG. 4 illustrates an aspect of an embodiment of the method of the present invention comprising N. tobacum seedlings growing in 0.5×MSS nutrient medium in the first screening wherein (A) shows two seedlings from EMS-treated seeds growing in medium containing 4 mM lysine and 4 mM threonine, and (B) shows the seedlings from EMS-treated seeds growing in medium containing no lysine and threonine.

FIG. 4 shows a separate experiment screening using high lysine/threonine medium (4 mM threonine/lysine) for one-month-old M1 *N. tobacum* seedlings growing in Magenta Vessels containing 0.5×MSS nutrient medium in the first screening (i.e. medium plus lysine and threonine). FIG. 4A shows two seedlings from EMS-treated seeds growing in a Magenta Vessel containing 4 mM lysine and 4 mM threonine. FIG. 4B shows the seedlings from EMS-treated seeds growing in a Magenta Vessel containing no lysine and threonine. As seen for the experiment shown in FIG. 3, seeds treated with EMS and selected in threonine/lysine media show resistance to these agents as M1 chimeric plants.

EXAMPLE 2

The amino acid profiles of several *N. tobacum* lines resistant to threonine and lysine were quantified. As shown in Table 2, novel lines which produce at least 120 nmoles of total amino acids per milligram dry weight in cured leaf were generated using the selection method. This represents at least up to a 2 fold increase in total free amino acids production over unmodified flue-cured *N. tobacum* parent, which normally yields a maximum of about 50 to 60 nmoles/mg.

These novel lines of *N. tobacum* also produced unusually high levels of individual amino acids in flue-cured tobacco leaves. Specifically, these novel plant lines produced 0.53, 0.73, and 1.36 nmoles of free threonine per milligram of dry leaf weight of flue-cured leaf material. This represents a 3 to 6 fold increase in free threonine production over the unmodified *N. tobacum* parent line.

Although the method relies on feedback inhibition of lysine and threonine synthesis, above-average amounts of other amino acids produced. Thus, the cell lines produced 29.64, 37.42, and 38.45 nmoles of free asparagine per milligram of dry leaf weight of flue-cured leaf material. This represents a 3 to 4 fold increase in free asparagine production over unmodified *N. tobacum* parent line.

Additionally, for flue-cured leaves, the novel lines of *N. tobacum* that produced a 260% to 444% increase in free glutamine, a 182% to 321% increase in free glutamic acid, a 79% to 168% increase in free serine, a 72% to 184% increase in free aspartic acid, a 75% to 113% increase in free leucine, a 45% to 136% increase in free isoleucine, a 153% to 361% increase in free phenylalanine, a 129% to 231% increase in free lysine, and a 33% to 642% increase in free arginine, a 235% to 374% increase in free histidine, an approximately 140% increase in free tyrosine, and an approximately 100% increase in free glycine (Table 2).

A deposit of seeds from a modified line of *N. tobacum* made by the methods of the invention (strain 120B derived from parent line K-326 and described in Table 2) was made on Aug. 29, 2001, to the American Type Culture Collection (ATCC, 10801 University Blvd., Manassas, Va. 20110-2209), under conditions prescribed by the Budapest Treaty. The ATCC accession number for the deposited strain is PTA-3673.

TABLE 2

Free Amino Acid in Flue-Cured Leaves of Different Lines of *Nicotiana tobacum*

| Amino Acids | Control K326 (nmole/mg) | 24-1B (nmole/mg) | 24-1B (% control) | 24-4 (nmole/mg) | 24-4 (% control) | 120B (nmole/mg) | 120B (% control) |
|---|---|---|---|---|---|---|---|
| Aspartic acid | 1.48 | 3.22 | 217 | 2.56 | 172 | 4.22 | 284 |
| Threonine | 0.22 | 0.73 | 333 | 0.53 | 244 | 1.36 | 623 |
| Serine | 0.64 | 1.41 | 220 | 1.15 | 179 | 1.72 | 268 |
| Asparagine | 8.22 | 37.42 | 455 | 29.64 | 361 | 38.45 | 468 |
| Glutamic acid | 0.53 | 2.23 | 421 | 1.50 | 282 | 1.56 | 295 |
| Glutamine | 6.68 | 37.34 | 544 | 24.70 | 360 | 28.31 | 412 |
| Proline | 30.79 | 51.14 | 166 | 51.28 | 167 | 38.60 | 125 |
| Glycine | 0.25 | 0.51 | 200 | 0.44 | 174 | 0.48 | 189 |
| Alanine | 3.39 | 6.12 | 181 | 5.56 | 167 | 5.25 | 155 |
| Cysteine | 1.01 | 0.77 | 76 | 1.14 | 112 | 0.85 | 84 |
| Methionine | 0.43 | 0.56 | 130 | 0.47 | 109 | 0.40 | 92 |
| Isoleucine | 0.04 | 0.10 | 236 | 0.06 | 145 | 0.08 | 200 |
| Leucine | 0.09 | 0.19 | 204 | 0.16 | 175 | 0.19 | 213 |
| Tyrosine | 0.18 | 0.25 | 139 | 0.19 | 106 | 0.45 | 245 |
| Phenylalanine | 0.20 | 0.75 | 374 | 0.51 | 253 | 0.92 | 461 |
| Lysine | 0.14 | 0.48 | 331 | 0.42 | 290 | 0.33 | 229 |
| Histidine | 0.46 | 2.20 | 474 | 1.63 | 350 | 1.55 | 335 |
| Arginine | 0.03 | 0.12 | 358 | 0.05 | 133 | 0.26 | 742 |
| Total | 54.99 | 145.55 | 265 | 122.07 | 222 | 125.00 | 227 |

In some cases, the actual values for amino acid content will depend on the processing and developmental stage of the tobacco. Tables 3 and 4 show values of free amino acids in green leaves of the modified *N. tobacum* lines. Generally, amino acid values are higher in flue cured material than in green leaves from the same line, presumably due to degradation of proteins caused by curing. Still, tobacco lines comprising increased amino acids in green leaves are produced by the methods of the invention. For example, tobacco lines 120 BW and 120 BR comprising at least 15.8 and 20.1 nmole/mg green leaf weight, or a 6 to almost 8 fold increase in threonine, respectively, are produced (Table 3). Similar results were found for *N. tobacum* grown in the field. Thus, it was found that for some lines (e.g. 120B) certain amino acids were reduced compared to the parent control for green leaves. Still, in other cases (see e.g. 120B line; Table 4) the relative increase was maintained (isoleucine, leucine, tyrosine, and lysine) or higher (glycine and methionine) in the green leaves relative to the flue-cured.

TABLE 3

Free amino acid in green leaves of different lines of
N. tobacum grown in growth chamber

| | Tobacco Lines | | | | | | |
|---|---|---|---|---|---|---|---|
| | K326 (control) | 24-4 | | 120 BW | | 120 BR | |
| Amino Acids | n mole/mg | n mole/mg | % of control | n mole/mg | % of control | n mole/mg | % of control |
| Aspartic acid | 4.77 | 5.97 | 125 | 4.18 | 87 | 4.96 | 104 |
| Threonine | 2.55 | 3.61 | 142 | 15.81 | 621 | 20.16 | 792 |
| Serine | 3.09 | 3.06 | 99 | 2.95 | 95 | 3.40 | 110 |
| Asparagine | 5.77 | 10.59 | 184 | 4.22 | 73 | 5.91 | 102 |
| Glutamic acid | 3.48 | 4.69 | 135 | 3.43 | 99 | 4.78 | 137 |
| Glutamine | 6.23 | 11.31 | 182 | 3.31 | 53 | 5.67 | 91 |
| Proline | 27.46 | 39.98 | 146 | 25.34 | 92 | 25.53 | 93 |
| Glycine | 1.80 | 1.75 | 97 | 1.79 | 100 | 1.43 | 79 |
| Alanine | 2.94 | 2.72 | 92 | 2.37 | 80 | 2.37 | 81 |
| Cysteine | 0.78 | 0.92 | 117 | 0.82 | 105 | 0.86 | 110 |
| Methionine | 0.36 | 0.48 | 135 | 0.41 | 114 | 0.29 | 80 |
| Isoleucine | 0.92 | 1.43 | 156 | 1.26 | 137 | 1.06 | 116 |
| Leucine | 2.61 | 3.71 | 142 | 2.97 | 114 | 2.15 | 82 |
| Tyrosine | 1.60 | 2.57 | 161 | 1.65 | 103 | 1.54 | 97 |
| Phenylalanine | 1.16 | 2.17 | 188 | 1.44 | 125 | 0.88 | 76 |
| Lysine | 2.72 | 3.04 | 112 | 2.84 | 104 | 2.59 | 95 |
| Histidine | 7.47 | 12.02 | 161 | 5.90 | 79 | 6.61 | 89 |
| Arginine | 1.44 | 1.91 | 133 | 1.78 | 124 | 1.93 | 134 |
| Total | 77.14 | 111.92 | 145 | 82.45 | 107 | 92.12 | 119 |

TABLE 4

Free amino acid in green leaves of different lines of
Nicotiana tobacum grown in the field.

| | Tobacco Lines | | | | |
|---|---|---|---|---|---|
| | K326 (control) | 24-4 | | 120B | |
| Amino Acids | n mole/mg | n mole/mg | % of control | n mole/mg | % of control |
| Aspartic acid | 1.15 | 1.22 | 106 | 1.71 | 148 |
| Threonine | 2.01 | 1.92 | 95 | 8.81 | 438 |
| Serine | 1.40 | 1.12 | 80 | 2.79 | 198 |
| Asparagine | 1.67 | 1.70 | 102 | 2.53 | 151 |
| Glutamic acid | 0.42 | 0.50 | 119 | 0.72 | 173 |
| Glutamine | 0.80 | 1.68 | 109 | 1.47 | 184 |
| Proline | 10.43 | 8.54 | 82 | 8.53 | 82 |
| Glycine | 1.33 | 1.15 | 87 | 3.05 | 230 |
| Alanine | 12.06 | 10.58 | 88 | 15.96 | 132 |
| Cysteine | 0.71 | 0.64 | 90 | 0.74 | 104 |
| Methionine | 0.35 | 0.20 | 57 | 0.81 | 235 |
| Isoleucine | 1.08 | 1.28 | 118 | 2.55 | 236 |
| Leucine | 2.32 | 1.78 | 77 | 5.05 | 218 |
| Tyrosine | 0.81 | 0.80 | 98 | 1.91 | 235 |
| Phenylalanine | 1.13 | 1.13 | 100 | 2.28 | 201 |
| Lysine | 1.96 | 2.04 | 104 | 4.52 | 231 |
| Histidine | 0.68 | 1.28 | 190 | 1.65 | 243 |
| Arginine | 1.20 | 1.32 | 110 | 2.76 | 229 |
| Total | 41.51 | 38.88 | 94 | 67.84 | 163 |

EXAMPLE 3

Figure 5:
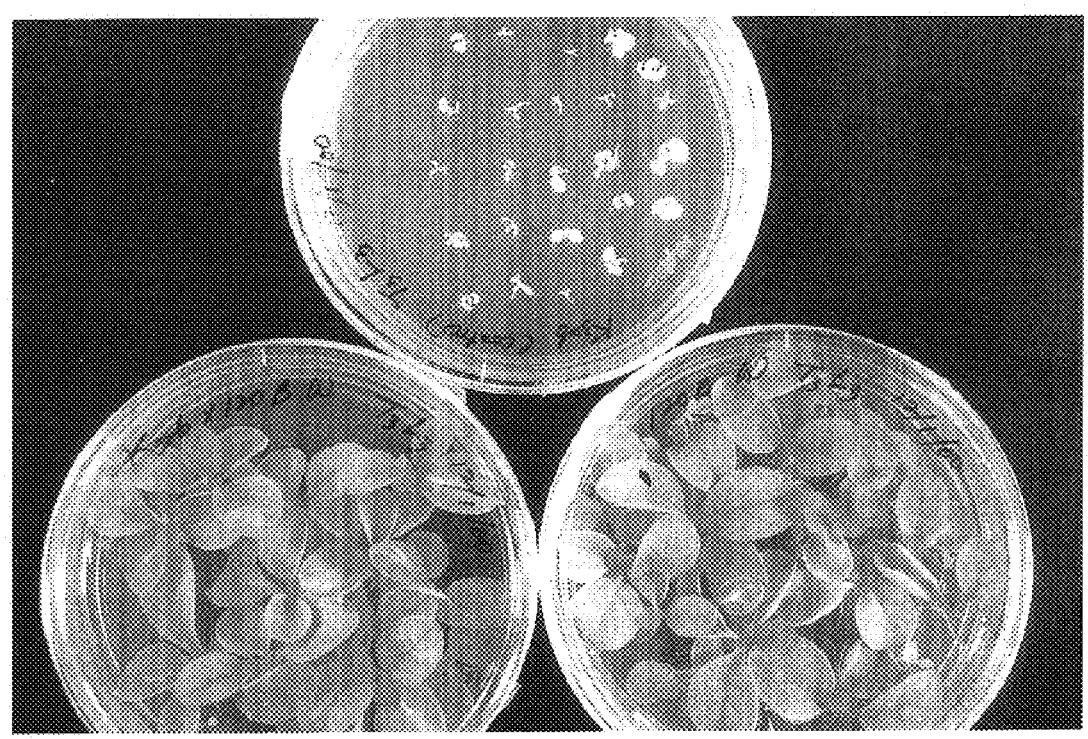
FIG. 5 illustrates an aspect of an embodiment of the method of the present invention comprising new lines of N. tobacum seedlings growing in petri dishes containing MS medium containing 3 mM lysine and 3 mM threonine, wherein the dish at the top is parent line K326, the plate at the right is new line 120BW, a high threonine producer, and the plate at the left is the F1 progeny of K326 and 120BW.

It was found that resistance to threonine/lysine inhibition of protein synthesis is a dominant trait. FIG. 5 shows new lines of N. tobacum seedlings growing in petri dishes containing MS medium containing 3 mM lysine and 3 mM threonine. At the top, is the K326 N. tobacum line, which is a non-mutagenized parent of high threonine producer 120BW. At the right is the 120BW line, and at the left, is the F1 progeny of K326 (the non-mutagenized parent) and 120BW (the high threonine producer). It was found that there are no F1 progeny which did not show resistance to lysine and threonine inhibition.

EXAMPLE 4

Since the sensitivity of AK to feedback inhibition is the major limiting factor for threonine synthesis, mutations conferring resistance to lysine plus threonine generally occur in the coding DNA sequences of the AK isoenzymes resulting in structurally modified enzymes, rather than enzymes with altered expression patterns. As the genes encoding AK s are apparently expressed in all plant tissues, amino acid overproduction is virtually constitutive. Constitutive synthesis of threonine at high level may be toxic to the cells, resulting in phenotypic alteration and sterility (Frankard, V., el al., 1992). However, Bright, S. W. J., et al. (1982a) found that the agronomic performance of barley mutant with a 100 times increase of threonine was not markedly affected when compared with the parent.

Figure 6:
FIG. 6 illustrates an aspect of an embodiment of the method of the present invention comprising a sterile M1 plant with a threonine concentration 150 times that of the parent control.

In most cases, individual amino acids were increased 2 to 10 fold in EMS treated lines with no evidence of toxicity. In addition, the modified lines were visually indistinguishable from the K326 parent. In some cases, however, much higher increases in specific amino acids resulted. For example, FIG. 6 shows a plant in which the concentration of threonine was about 150 times as much as that in K326, the parent control. Although generally healthy, this plant was stunted and sterile.

EXAMPLE 5

Figure 7:
FIG. 7 illustrates an aspect of an embodiment of the method of the present invention comprising a chimeric M1 plant with an alteration in leaf morphology.

Generally, N. tobacum lines comprising high levels of amino acid synthesis were morphologically indistinguishable from the parent lines. FIG. 7, however, shows a chimeric M1 plant with an alteration in leaf morphology occurring at very early stage of the plant development. The presence of mutagenized cells at very early developmental stages substantiates that the altered cells in the M1 chimera which are insensitive to high levels of threonine and lysine in the growth medium or soil provide enough methionine to the cells that have normal aspartate kinase to support the growth of the whole chimeric plant under selective conditions.

The methods of the present invention provide a rapid and economical mutagenesis method for developing plant lines having increased amino acids. In an embodiment, the plant is tobacco. The invention provides a method whereby mutagenized tobacco seeds are allowed to germinate under non-selective conditions, and then chimeric plants at least partially comprising a phenotype resistant to threonine/lysine inhibition of protein synthesis are selected. Included in the present invention are modified tobacco lines having an increase in at least one, and generally more than one, amino acid. Of specific value are tobacco lines having increased threonine. These high threonine tobacco lines can be used as germplasm to develop new tobacco varieties with altered amino acid profiles. These high threonine tobacco lines can also be mixed with other strains of tobacco to produce a blend having improved taste and aroma. All references cited herein are incorporated by reference in their entirety.

What is claimed is:

1. A method for producing a modified tobacco line comprising an alloploid genome having an altered phenotype of an increased amount of threonine as compared to an unmodified parent alloploid tobacco line comprising the steps of:
   (a) incubating tobacco seeds in a solution comprising a mutagen;
   (b) washing the seeds free of the mutagen;
   (c) germinating the seeds and growing M1 seedlings;
   (d) adding a medium comprising threonine and lysine to the M1 seedlings;
   (e) growing the M1 seedlings to generate at least one M1 chimeric plant comprising M2 seeds, wherein the threonine and lysine select for a chimeric M1 plant that at least partially comprises the altered phenotype of an increase in threonine, and wherein the M2 seeds from the chimeric plant comprise non-mutagenized M2 seeds and mutagenized M2 seeds; and
   (f) germinating the M2 seeds in medium comprising threonine and lysine to select for M2 plants comprising the altered phenotype of an increase of at least a 2 to 150 fold in threonine as compared to the unmodified alloploid parent tobacco line.

2. The method of claim 1, further comprising the steps of:
   growing the M2 plants to generate M3 seeds, wherein at least one of the M2 plants is a heterozygote and at least one of the M2 plants is a homozygote for a mutation conferring the ability to grow in the presence of increased threonine and lysine; and
   incubating the M3 seeds in medium comprising threonine and lysine to identify at least one homozygote M2 plant.

3. The method of claim 1, wherein the medium comprising threonine and lysine is added to the M1 seedlings 7 to 14 days after germination.

4. The method of claim 1, wherein the medium comprising threonine and lysine is added to the M1 seedlings 10 days after germination.

5. The method of claim 1, wherein the mutagen comprises ethyl methanesulfonate (EMS).

6. The method of claim 1, wherein the modified tobacco line comprises at least a 5 to 150 fold increase in threonine.

7. The method of claim 1, wherein the modified tobacco line comprises at least plants having a 150 fold increase in threonine.

8. A modified tobacco plant comprising at least a 2 to 150 fold increase in threonine as compared to an unmodified alloploid parent tobacco line, wherein the genome of the modified tobacco plant comprises an alloploid genome having a mutation that exhibits a dominant phenotype of resistance to growth in the presence of lysine or threonine.

9. The plant of claim 8, further comprising at least a 5 to 150 fold increase in threonine.

10. The plant of claim 8, further comprising at least a 150 fold increase in threonine.

11. The plant of claim 8, wherein the plant species comprises *Nicotiana tobacum*.

* * * * *

UNITED STATES PATENT AND TRADEMARK OFFICE
CERTIFICATE OF CORRECTION

PATENT NO. : 7,173,170 B2
APPLICATION NO. : 10/463449
DATED : February 6, 2007
INVENTOR(S) : Wennuan Liu et al.

It is certified that error appears in the above-identified patent and that said Letters Patent is hereby corrected as shown below:

Column 13, Line 44 the word "hetergzygotes," should read --heterozygotes--

Column 17, Line 65, the word "Bamstead" should read --Barnstead--

Column 24, Line 30, the claims,
"8. A modified tobacco plant comprising at least a 2 to 150 fold increase in threonine as compared to an unmodified alloploid parent tobacco line, wherein the genome of the modified tobacco plant comprises an alloploid genome having a mutation that exhibits a dominant phenotype of resistance to growth in the presence of lysine or threonine.
9. The plant of claim 8, further comprising at least a 5 to 50 fold increase in threonine.
10. The plant of claim 8, further comprising at least a 150 fold increase in threonine.
11. The plant of claim 8, wherein the plant species comprises *Nicotiana tobacum*."
should read:
--8. The method of claim 1, wherein the tobacco line comprises the species *Nicotiana tobacum*.
9. A modified tobacco plant comprising at least a 2 to 150 fold increase in threonine as compared to an unmodified alloploid parent tobacco line, wherein the genome of the modified tobacco plant comprises an alloploid genome having a mutation that exhibits a dominant phenotype of resistance to growth in the presence of lysine or threonine.
10. The plant of claim 9, further comprising at least a 5 to 50 fold increase in threonine.
11. The plant of claim 9, further comprising at least a 150 fold increase in threonine.
12. The plant of claim 9, wherein the plant species comprises *Nicotiana tobacum*--

Column 24, Line 28 the phrase "comprises at least plants having a" should read --comprises plants having at least a--

Signed and Sealed this

Seventh Day of July, 2009

JOHN DOLL
*Acting Director of the United States Patent and Trademark Office*